United States Patent [19]

Kempf

[11] Patent Number: 5,130,468

[45] Date of Patent: Jul. 14, 1992

[54] PROCESS FOR THE PREPARATION OF A DIPEPTIDE ISOSTERE

[75] Inventor: Dale J. Kempf, Libertyville, Ill.

[73] Assignee: Abbott Laboratories, Abbott Park, Ill.

[21] Appl. No.: 698,019

[22] Filed: May 9, 1991

[51] Int. Cl.$^5$ ............................................. C07C 229/00
[52] U.S. Cl. .................................. 560/155; 556/442; 556/420; 530/323; 560/169; 560/29; 560/115; 560/148; 562/500; 549/419; 558/32
[58] Field of Search .............. 556/442, 420; 530/323; 560/169, 155, 29, 115, 148, 160; 514/359; 562/500; 549/419; 558/32

[56] References Cited

PUBLICATIONS

Hann, et al., J. Chem. Soc. Perkin I 307 (1982).
Cox, et al., J. Chem. Soc. Chem. Comm. 799 (1980).
Miles, et al., J. Chem. Soc. Perkin Trans. I 2299 (1985).
Whitesell, et al., Chirality, 1 89 (1989).
Shue, et al., Tet. Lett. 28, 3225 (1987).
Shue, et al., Tet. Lett. 29 4041 (1988).
Spaltenstein, et al., Tet. Lett. 27 2095 (1986).
Spaltenstein, et al., J. Org. Chem. 52 3759 (1987).
Hanson, et al., J. Org. Chem. 50 5399 (1985).
Ibuka, et al., Angew. Chem. Int. Ed. Engl. 29 (7) 801 (1990).
Wang, et al., Abstract ORGN #60.

*Primary Examiner*—Jose G. Dees
*Assistant Examiner*—Joseph Conrad
*Attorney, Agent, or Firm*—Steven R. Crowley

[57] ABSTRACT

A process and intermediates useful for the preparation of (E)-alkene dipeptide isosteres are disclosed.

2 Claims, No Drawings

PROCESS FOR THE PREPARATION OF A DIPEPTIDE ISOSTERE

TECHNICAL FIELD

The present invention relates to a process and intermediates useful for the preparation of (E)-alkene dipeptide isosteres.

BACKGROUND OF THE INVENTION

Dipeptide mimics wherein the amide bond (—C(O)NH—) is replaced by a trans olefin

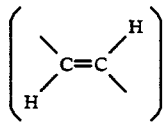

are commonly employed as isosteric replacements for a dipeptide moiety in peptidyl enzyme inhibitors or in analogs of endogenous peptidyl ligands. Various methods have been disclosed for the preparation of such olefinic dipeptide isosteres. (See Shue, et al., Tet. Lett. 28 3225 (1987); Shue, et al., Tet Lett. 29 4041 (1988); Spaltenstein, et al., Tet. Lett. 27 2095 (1986); Spaltenstein, et al., J. Org. Chem. 52 3759 (1987); Hann, et al., J. Chem. Soc. Perkin I 307 (1982); Cox, et al., J. Chem. Soc. Chem. Comm. 799 (1980); Miles, et al., J. Chem. Soc. Perkin Trans. I 2299 (1985); Whitesell, et al., Chirality 1 89 (1989); Hanson, et al., J. Org. Chem. 50 5399 (1985)). However, there remains a need for a method for preparing olefinic dipeptide isosteres wherein the $\alpha$ and $\delta$ side chains can be introduced in a stereocontrolled manner.

DISCLOSURE OF THE INVENTION

The present invention relates to a process for the preparation of the compound of formula 2. The process of this invention is shown in Scheme 1.

According to the process of Scheme 1, a diastereomerically pure compound of the formula 1a-d ($R_1$ is loweralkyl, cycloalkyl, cycloalkylalkyl, aryl, arylalkyl, alkoxyalkyl or thioalkoxyalkyl; $R_2$ is an N-protecting group (for example, t-butyloxycarbonyl, benzyloxycarbonyl or trichloroethoxycarbonyl and the like); $R_3$ is loweralkyl, benzyl, substituted benzyl wherein the phenyl ring is substituted with one, two or three substituents independently selected from loweralkyl, alkoxy and halo, or $R_3$ is a silyl group (for example, t-butyldimethylsilyl, t-butyldiphenylsilyl, triethylsilyl or triisopropylsilyl and the like); and $R_4$ is loweralkyl, haloalkyl, phenyl or substituted phenyl wherein the phenyl ring is substituted with loweralkyl or halo) is reacted with a Grignard reagent $R_6MgX$ ($R_6$ is loweralkyl, cycloalkyl, cycloalkylalkyl, aryl, arylalkyl, alkoxyalkyl or trialkylsilyloxyalkyl and X is halogen) in the presence of CuCN (from about 1 to about 50 mole %) in an inert solvent (for example, THF (tetrahydrofuran), diethyl ether or dimethoxyethane and the like) at a temperature of from about $-78°$ C. to about $20°$ C. to provide diastereomerically pure ($>95\%$ pure) 2a-d, respectively.

The diastereomerically pure compounds 1a and 1d can be prepared according to the process shown in Scheme 2. According to the process of Scheme 2, reaction of vinyl Grignard with the N-protected L-amino acid 3a in an inert solvent (for example, THF, diethyl ether or dimethoxyethane and the like) at a temperature of from about $-20°$ C. to about $60°$ C. provides 4a. Reduction of 4a (for example, with NaBH$_4$/CeCl$_3$, DIBAL, L-Selectride® or K-Selectride® and the like) in an inert solvent (for example, THF or methylene chloride and the like) at a temperature of from about $-100°$ C. to about $-20°$ C. provides a mixture of allylic alcohols 5a and 11a, in which 5a is the predominant isomer. Alcohol 5a can be separated by chromatography. Protection of the alcohol ($R_7$ is an O-protecting group, for example, tetrahydropyranyl or t-butyldimethylsilyl and the like) gives 6a. Oxidation of 6a (for example, by ozonolysis or OsO$_4$/NaIO$_4$) gives aldehyde 7a. Reaction of 7a with (CH$_3$)$_2$P(O)CH$_2$CO$_2$R$_3$ ($R_3$ is loweralkyl or benzyl) and a base (for example, NaH or a strong, non-nucleophilic base such as lithium diisopropylamide or lithium hexamethyldisilazide and the like) in an inert solvent (for example, THF or diethyl ether and the like) at a temperature of from about $0°$ C. to about $65°$ C. provides 8. Alternatively, 7a can be reacted with Ph$_3$P=CHCO$_2$R$_3$ in an inert solvent (for example, THF or toluene and the like) at a temperature of room temperature to $110°$ C. to provide 8a. Deprotection of the alcohol gives 9a. Reaction of 9a with R$_4$SO$_2$X (X is halogen, for example, Cl) in the presence of a base (for example, iPr$_2$NEt, Et$_3$N or N-methyl morpholine and the like) in an inert solvent (for example, CH$_2$Cl$_2$ or THF and the like) at a temperature of from about $-40°$ C. to about $0°$ C. provides 1a.

In a similar manner, N-protected D-amino acid 3b can be converted to 1d.

The diastereomerically pure compounds 1b and 1c can be prepared as shown in Scheme 3. Reduction of N-protected L-amino acid ester 10a (R$_8$ is loweralkyl or benzyl) for example, with DIBAL in an inert solvent (for example, toluene, benzene or THF and the like) at a temperature of from about $-100°$ C. to about $-50°$ C. provides the corresponding aldehyde. Without isolation, reaction in situ of the aldehyde with vinyl Grignard provides a mixture of 11a and 5a, in which 11a is the predominant isomer. Alcohol 11a can be separated by chromatography. Compound 11a can then be converted to 1b using the method outlined in Scheme 2 for converting 5a to 1a.

In a similar manner, N-protected D-amino acid ester 10b can be converted to 1c.

An alternative method for preparing 15a is shown in Scheme 4. N-protected oxazolidine 16a can be prepared from 11a by acetal formation, followed by oxidation. Compound 16a is reacted with (CH$_3$O)$_2$P(O)CH$_2$CO$_2$R$_3$ and a base (for example, NaH or lithium diisopropylamide and the like) in an inert solvent (for example, THF or diethyl ether and the like) at a temperature of from about $0°$ C. to about $60°$ C. to provide 17a. Alternatively, 16a can be reacted with Ph$_3$P=CHCO$_2$R$_3$ in an inert solvent (for example, THF or toluene and the like) at a temperature of room temperature to $110°$ C. to provide 17a. Deprotection under acidic conditions (for example, p-toluenesulfonic acid in ethanol or the like) provides 15a, which can be converted to 1b as outlined above.

An alternative preparation of 4a is shown in Scheme. N-protected L-amino acid 3a is converted to the N-alkoxy amide 18a. Reaction of the amide 18a with vinyl Grignard in an inert solvent (for example, THF or diethyl ether and the like) at a temperature of from about $0°$ C. to about $65°$ C. provides 4a.

In a similar manner, 4b can be prepared from 3b.

Lastly, Scheme 6 illustrates an alternative preparation of 1a from 5a. Reaction of 5a with $R_4SO_2X$ in the presence of a base (for example, $iPr_2NEt$, $Et_3N$ or N-methyl morpholine and the like) in an inert solvent (for example, $CH_2Cl_2$ or THF and the like) at a temperature of from about $-40°$ C. to about $0°$ C. provides 19a. Ozonolysis, followed by reaction with $Ph_3P=CHCO_2R_3$ in an inert solvent (for example, THF or toluene and the like) at a temperature of room temperature to $110°$ C., provides 1a.

In a similar manner, 5b, 11a and 11b can be converted to 1d, 1b and 1c, respectively.

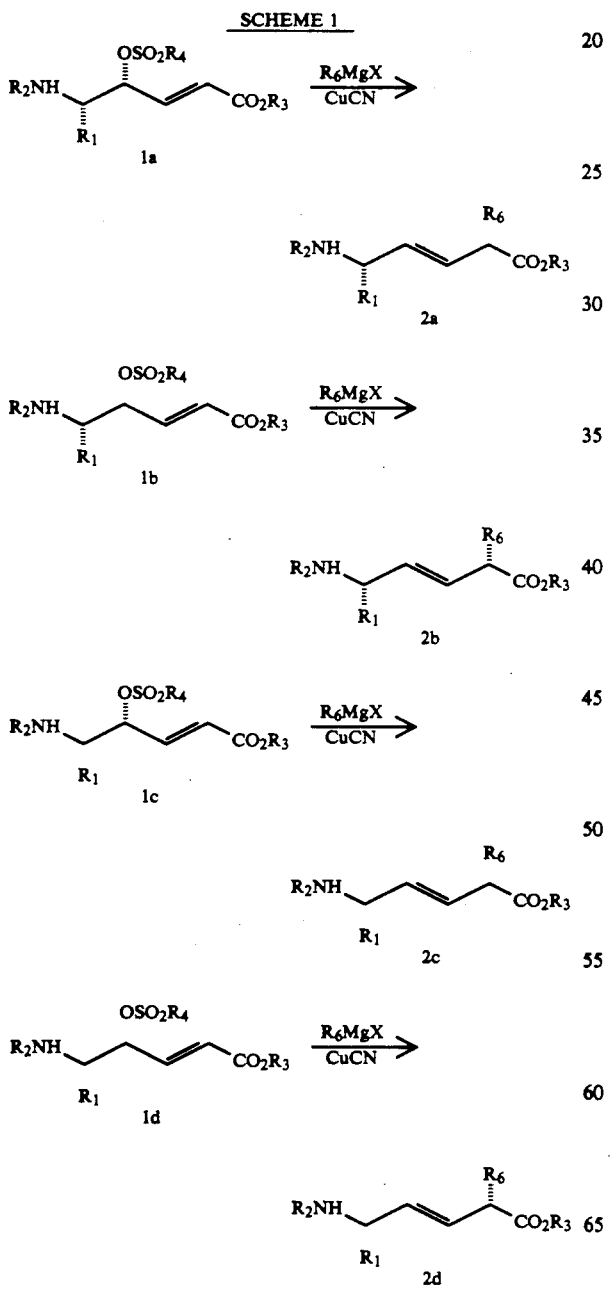

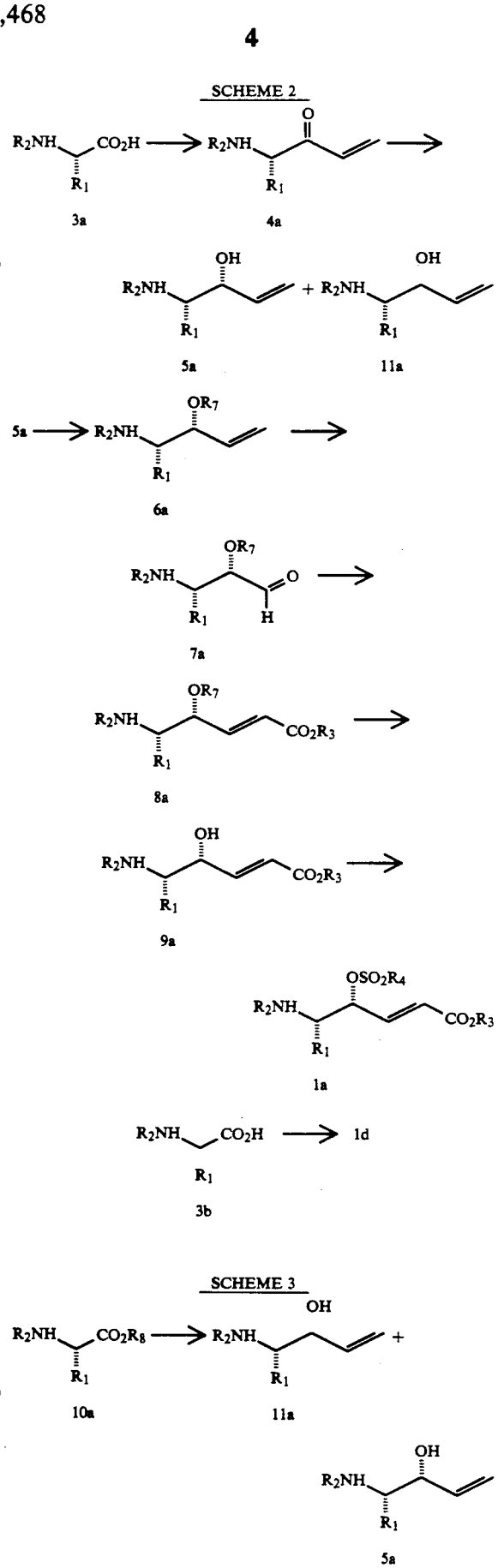

5,130,468
SCHEME 3
-continued
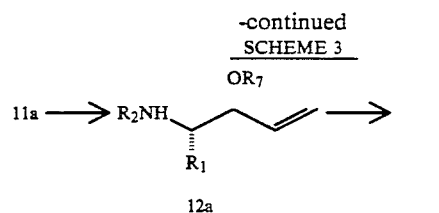
12a
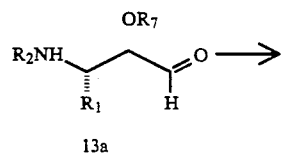
13a
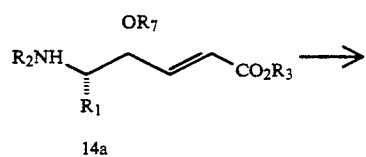
14a
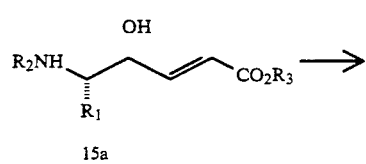
15a
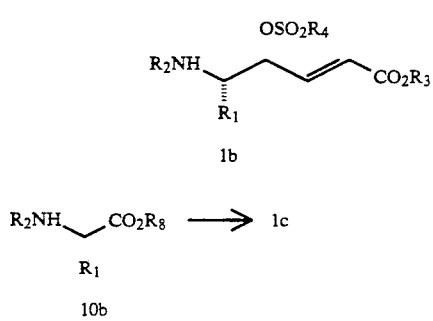
1b
10b → 1c
SCHEME 4
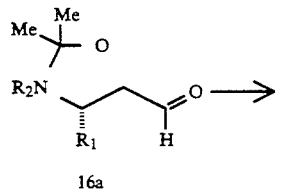
16a
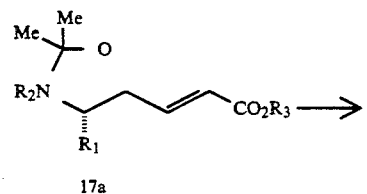
17a
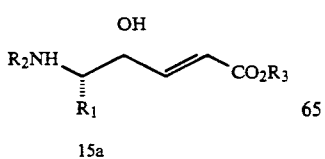
15a
SCHEME 5
3a
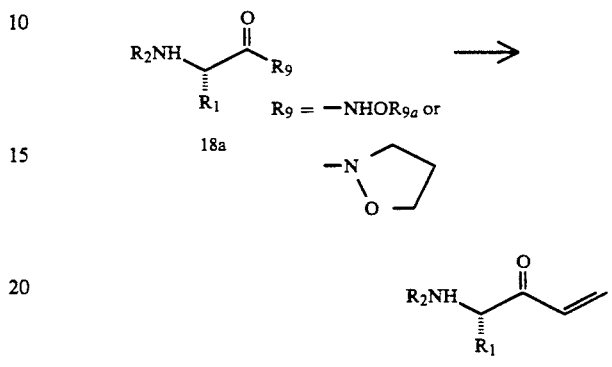
18a
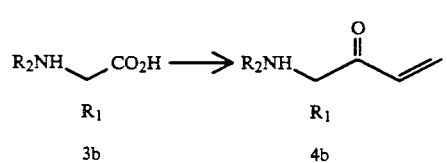
3b → 4b
SCHEME 6
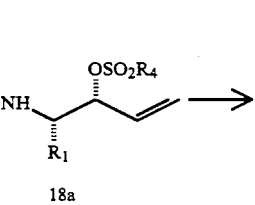
5a
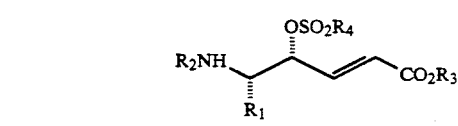
18a
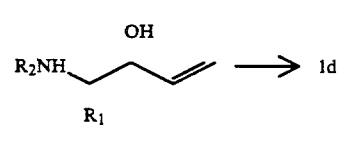
1a
5b → 1d
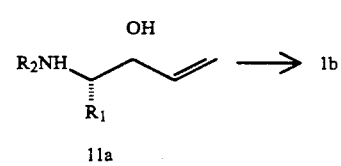
11a → 1b -continued
SCHEME 6

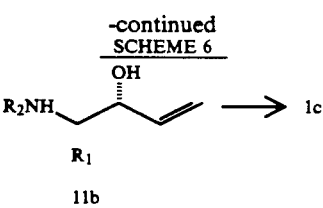

11b

A particularly useful intermediate for the process of this invention includes a substantially pure (2R,5S), (2R,5R), (2S,5S) or (2S,5R) diastereomer of the compound of the formula:

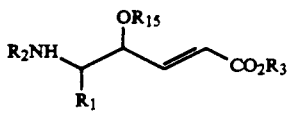

wherein $R_1$ is loweralkyl, cycloalkyl, cycloalkylalkyl, aryl, arylalkyl, alkoxyalkyl or thioalkoxyalkyl; $R_2$ is an N-protecting group; $R_3$ is loweralkyl, benzyl, substituted benzyl wherein the phenyl ring is substituted with one, two or three substituents independently selected from loweralkyl, alkoxy and halo or $R_3$ is t-butyldimethylsilyl, t-butyldiphenylsilyl, triethylsilyl or triisopropylsilyl; and $R_{15}$ is hydrogen, an O-protecting group or —$SO_2R_4$ wherein $R_4$ is loweralkyl, haloalkyl, phenyl or substituted phenyl wherein the phenyl ring is substituted with loweralkyl or halo.

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "cycloalkyl" as used herein refers to an alicyclic ring having 3 to 7 carbon atoms including, but not limited to, cyclopropyl, cyclopentyl, cyclohexyl and the like.

The term "cycloalkylalkyl" as used herein refers to a cycloalkyl residue appended to a loweralkyl radical and includes, but is not limited to, cyclohexylmethyl and cyclopentylmethyl.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, alkoxy, thioalkoxy and halo.

The term "arylalkyl" as used herein refers to an aryl group appended to a loweralkyl radical, including, but not limited to benzyl, phenethyl, 1-naphthylmethyl, 2-naphthylmethyl and the like.

The term "halogen" or "halide" as used herein refers to F, Cl, Br or I.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The terms "alkoxy" and "thioalkoxy" as used herein refer to $R_{20}O—$ and $R_{20}S—$, respectively, wherein $R_{20}$ is a loweralkyl group or benzyl.

The terms "alkoxyalkyl" and "thioalkoxyalkyl" as used herein refer to a loweralkyl radical to which is appended an alkoxy group or a thioalkoxy group, respectively.

The term "trialkylsilyloxyalkyl" as used herein refers to a loweralkyl radical to which is appended a group $(R_{21})_3SiO—$ wherein at each occurrence $R_{21}$ is independently selected from loweralkyl.

The term "N-protecting group" or "N-protected" as used herein refers to those groups intended to protect an amino group against undesirable reactions during synthetic procedures. In addition, the N-protecting group does not itself react under the conditions of the synthetic procedure being used. Commonly used N-protecting groups are disclosed in Greene, "Protective Groups In Organic Synthesis," (John Wiley & Sons, New York (1981)), which is hereby incorporated by reference. Particulary useful N-protecting groups comprise carbamates, for example, t-butyloxycarbonyl (Boc), benzyloxycarbonyl (Cbz) or trichloroethoxycarbonyl (Troc) and the like.

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The following examples will serve to further illustrate the process of the invention.

EXAMPLE 1

(4S)-4-(t-Butyloxycarbonylamino)-5-phenyl-1-penten-3-one

Vinylmagnesium bromide (1M in tetrahydrofuran) was cooled under $N_2$ atmosphere to $-10°$ C. and treated in portions with 10 g (37.7 mmol) of N-(t-butyloxycarbonyl)-L-phenylalanine. The resulting solution was stirred at $-10°$ C. for 5 h, and poured into a rapidly stirring mixture of ice, 10% aqueous citric acid and ether. The mixture was separated, and the organic phase was washed sequentially with water, two portions of aqueous $NaHCO_3$, and saturated brine; dried over $MgSO_4$; and concentrated in vacuo. Silica gel chromatography of the residue using 4:1 hexane:ethyl acetate provided 3.63 g (35%) of the desired compound ($R_f$ 0.33, 3:1 hexane:ethyl acetate). $^1H$ NMR ($CDCl_3$) $\delta$ 1.41 (s, 9 H), 2.98 (dd, J=14, 6 Hz, 1 H), 3.15 (dd, J=14, 6 Hz, 1 H), 4.86 (q, J=8 Hz, 1 H), 5.23 (br d, 1 H), 5.85 (dd, J=9, 2 Hz, 1 H), 6.35 (dd, J=18, 2 Hz, 1 H), 6.45 (dd, J=18, 9 Hz, 1 H), 7.10 (br d, 2 H), 7.25 (m, 3 H). Mass spectrum: $(M+H)^+ = 276$.

Anal. Calcd for $C_{16}H_{21}NO_3$: C, 69.79; H, 7.69; N, 5.09. Found: C, 69.72; H, 7.65; N, 5.00.

EXAMPLE 2

(3R,4S)-4-(t-Butyloxycarbonylamino)-3-hydroxy-5-phenyl-1-pentene

A solution of 3.03 g (11 mmol) of the resultant compound of Example 1 in 120 ml of 1:1 dichloromethane:- methanol was cooled to 0° C., and treated with 4.10 g (11 mmol) of cerium(III) chloride heptahydrate. The resulting solution was immediately cooled to −78° and treated slowly with a solution of 0.63 g (16.5 mmol) of sodium borohydride in 15 ml of ethanol in such a way that the ethanolic solution was precooled by the side of the flask. After 1 h, the solution was quenched by addition of aqueous ammonium chloride, extracted with ether, washed sequentially with aqueous NaHCO$_3$ and saturated brine, dried over MgSO$_4$ and concentrated in vacuo to give a 4.7:1 ratio of diastereomeric products. Silica gel chromatography of the residue using 3:1 hexane:ethyl acetate provided 1.58 g (52%) of the pure desired compound (R$_f$0.35, 15% ethyl acetate in chloroform) as a white solid (m.p. 122°–124° C.), along with 0.22 g (7%) of (3R,4S)-4-(t-butyloxycarbonylamino)-3-hydroxy-5-phenyl-1-pentene. $^1$H NMR (CDCl$_3$) δ 1.37 (s, 9 H), 2.73 (dd, J=15, 9 Hz 1 H), 2.85 (dd J=15, 5 Hz, 1 H), 2.98 (m, 1 H), 3.98 (m, 1 H), 4.24 (m, 1 H), 4.58 (br, 1 H), 5.29 (dt, J=10, 1.5 Hz, 1 H), 5.38 (dt, J=17, 1.5 Hz, 1 H), 5.94 (ddd, J=17, 10, 6 Hz, 1 H), 7.2–7.3 (m, 5 H).

Anal. Calcd for C$_{16}$H$_{23}$NO$_3$: C, 69.29; H, 8.36; N, 5.05. Found: C, 69.31; H, 8.34; N, 4.98.

EXAMPLE 3

(3R,4S)-4-(t-Butyloxycarbonylamino)-5-phenyl-3-(3,4,5,6-tetrahydropyran-2-yl)oxy-1-pentene A solution of 1.01 g (3.65 mmol) of the resultant compound of Example 3 in 10 ml of dichloromethane was treated with 0.43 ml (4.7 mmol) of 2-(4 H)-dihydropyran and 0.18 g (0.73 mmol) of pyridinium p-toluenesulfonate. The resulting solution was stirred at ambient temperature for 16 h, diluted with ether, washed sequentially with 10% citric acid, water, and aqueous NaHCO$_3$, dried over MgSO$_4$, and concentrated in vacuo. The residue was purified by silica gel chromatography using 5:1 heaxne:ethyl acetate to provide 1.08 g (82%) of the desired compound (R$_f$ 0.26, 5:1 hexane:ethyl acetate). $^1$H NMR spectrum showed a 1:1 mixture of diastereomers. Mass spectrum: (M+H)$^+$=3.62.

Anal. Calcd for C$_{21}$H$_{31}$NO$_4$: C, 69.78; H, 8.64; N, 3.87. Found: C, 69.47; H, 8.55; N, 3.81.

EXAMPLE 4

(2R,3S)-3-(t-Butyloxycarbonylamino)-4-phenyl-2-((3,4,5,6-tetrahydropyran-2-yl)oxy)butanal A solution of 0.5 g (1.4 mmol) of the resultant compound of Example 3 in 15 ml of dichloromethane was cooled to −78° C. A stream of O$_3$ in air was bubbled through the solution until the blue color persisted. A stream of N$_2$ gas was subsequently bubbled through the solution until the blue color was discharged. The resulting solution was transferred via cannula to a precooled (−25° C.) suspension of 0.9 g of zinc dust and 1.2 ml of glacial acetic acid in aqueous methanol. The mixture was allowed to warm to ambient temperature for 2 h, after which it was treated with saturated brine, extracted with dichloromethane, dried over MgSO$_4$, and concentrated at 0° C. in vacuo. The crude desired product (R$_f$0.58, 2:1 hexane:ethyl acetate) was used without further purification.

EXAMPLE 5 trans-(4R,5S)-Methyl 5-(t-Butyloxycarbonylamino)-6-phenyl-4-((3,4,5,6-tetrahydropyran-2-yl)oxy)-2-hexenoate Sodium hydride (0.061 g) was washed with hexane under N$_2$ atmosphere, then treated with 2 ml of tetrahydrofuran. The resulting suspension was cooled under N$_2$ to 0° C. and treated with a solution of 0.22 ml of trimethylphosphono-acetate in 3 ml of tetrahydrofuran. After being stirred for 10 min, the solution was treated with a solution of the crude resultant compound of Example 4 in 3 ml of tetrahydrofuran. The resulting solution was stirred at ambient temperature for 2 h, quenched with saturated aqueous ammonium chloride, extracted with ether, washed with saturated brine, dried over Na$_2$SO$_4$, and concentrated in vacuo. Silica gel chromatography of the residue using 5:1 hexane:ethyl acetate provided 0.35 g (60%) of the desired compound (R$_f$0.45, 2:1 hexane:ethyl acetate). $^1$H NMR spectrum showed a 1:1 mixture of diastereomers. Mass spectrum: (M+H)$^+$=420.

EXAMPLE 6 trans-(4R,5S)-Methyl 5-(t-Butyloxycarbonylamino)-4-hydroxy-6-phenyl-2-hexenoate

A solution of 0.35 g (0.84 mmol) of the resultant compound of Example 5 and 0.21 g (0.84 mmol) of pyridinium p-toluenesulfonate in 10 ml of methanol was stirred at ambient temperature for 16 h. The resulting solution was concentrated in vacuo, and the residue was partitioned between ethyl acetate and saturated brine. The organic layer was washed with saturated brine, dried over Na$_2$SO$_4$, and concentrated in vacuo. The residue was purified by silica gel chromatography using 4:1 hexane:ethyl acetate to provide 0.20 g (71%) of the desired compound (R$_f$0.27, 2:1 hexane:ethyl acetate) as a white solid. $^1$H NMR (CDCl$_3$) δ 1.39 (s, 9 H), 2.75–2.9 (m 2 H), 3.77 (s, 3 H), 4.04 (m, 1 H), 4.46 (m, 1 H), 4.56 (m, 1 H), 5.06 (br d, 1 H), 6.19 (dd, J=15, 2 Hz, 1 H), 7.01 (dd, J=15, 5 Hz, 1 H), 7.25–7.45 (m, 5 H). Mass spectrum: (M+H)$^+$=336.

EXAMPLE 7 trans-(4R,5S)-Methyl 5-(t-Butyloxycarbonylamino)-4-(methanesulfonyloxy)-6-phenyl-2-hexenoate A solution of 0.44 g (1.3 mmol) of the resultant compound of Example 6 and 0.91 ml (5.2 mmol) of diisopropylethylamine in 20 ml of anhydrous dichloromethane was cooled under N$_2$ atmosphere to −20° C. and treated with 0.2 ml (2.6 mmol) of methanesulfonyl chloride. After 20 minutes, the mixture was treated with 10 % aqueous citric acid, extracted with methylene chloride, dried over sodium sulfate and concentrated in vacuo. Silica gel chromatography provided the desired product. $^1$H NMR (CDCl$_3$) δ 1.36 (s, 9 H), 2.73 (m, 1 H), 2.93 (dd, J=14, 5 Hz, 1 H), 3.06 (S, 3 H), 3.77 (s, 3 H), 4.18 (m, 1 H), 4.62 (s, 1 H), 5.47 (m, 1 H), 6.17 (dd, J=16, 2 Hz, 1 H), 6.90 (dd, J=16, 6 Hz, 1 H), 7.15–7.35 (m, 5 H).

EXAMPLE 8 trans-(2R,5S)-Methyl 2-Benzyl-5-(t-butyloxycarbonylamino)-6-phenyl-3-hexenoate Cuprous cyanide (5 mg) was placed in a flask which was flushed with $N_2$ gas. Anhydrous tetrahydrofuran (0.5 ml) was added, and the mixture was cooled under $N_2$ to 30° C. A solution of benzylmagnesium chloride (0.18 ml, 1.0M in diethyl ether) was added, and the mixture was stirred for 10 min to produce a yellow slurry. A solution of 30 mg (0.073 mmol) of the resultant compound of Example 7 in 1 ml of anhydrous tetrahydrofuran was subsequently added, and the resulting solution was stirred and allowed to warm to −10° C. over a period of 30 min. After addition of aqueous ammonium chloride, the mixture was extracted with ethyl acetate, washed with saturated brine, dried over $Na_2SO_4$, and concentrated in vacuo. Chromatography on silica gel using 6:1 hexane:ethyl acetate provided 25 mg (84%) of the desired compound ($R_f$ 0.71, 2:1 hexane:ethyl acetate). $^1$H NMR (CDCl$_3$) δ 1.41 (s, 9 H), 2.2-2.3 (m, 3 H), 3.04 (dd, J=13, 7 Hz, 1 H), 3.25 (q, J=7 Hz, 1 H), 3.61 (s, 3 H), 4.37 (m, 2 H), 5.39 (dd, J=15, 5 Hz, 1 H), 5.55 (dd, J=15, 8 Hz, 1 H), 7.05–7.15 (m, 4 H), 7.2–7.3 (m, 6 H). Mass spectrum: $(M+NH_4)^+ = 427$.

EXAMPLE 9

(3S,4S)-4-(t-Butyloxycarbonylamino)-3-hydroxy-5-phenyl-1-pentene

A solution of 10.25 g (36.7 mmol) Of N-(t-butyloxycarbonyl)phenylalanine methyl ester in 60 ml of toluene was cooled to −78° C. under inert atmosphere and treated dropwise over a period of 45 min with 35 ml (52.5 mmol) of diisobutylaluminum hydride in toluene. The resulting solution was stirred for 5 min, treated with 200 ml (200 mmol) of vinylmagnesium bromide, and allowed to warm to 0° C. for 16 h. The solution was subsequently quenched cautiously with methanol, treated with aqueous Rochelle salts, stirred for a few min, and filtered. The residue was digested several times with ethyl acetate and filtered; and the combined filtrates were washed with saturated brine, dried over MgSo$_4$, and concentrated. Silica gel chromatography using 20% ethyl acetate in hexane gave 5.46 g (54%) of the desired compound (m.p. 98°-100° C., $R_f$ 0.19, 3:1 hexane:ethyl acetate) along with 0.92 g (9%) of (3R,4S)-4-(t-butyloxycarbonylamino)-3-hydroxy-5-phenyl-1-pentene. $^1$H NMR (CDCl$_3$) δ 1.39 (s, 9 H), 2.27 (br, 1 H), 2.90 (AA', 2 H), 3.80 (m, 1 H), 4.11 (m, 1 H), 4.79 (m, 1 H), 5.19 (dt, J=11, 1.5 Hz, 1 H), 5.28 (dt, J=18, 1.5 Hz, 1 H), 5.90 (ddd, J=18, 11, 6 Hz, 1 H), 7.15–7.35 (m, 5 H). Mass spectrum: $(M+H)^+ = 2.76$.

EXAMPLE 10

(3S,4S)-4-(t-Butyloxycarbonylamino)-5-phenyl-3-(3,4,5,6-tetrahydropyran-2-yl)oxy-1-pentene A solution of 1 g (3.6 mmol) of the resultant compound of Example 9 in 10 ml of dichloromethane was treated with 0.43 ml (4.7 mmol) of 2-(4H)-dihydropyran and 0.18 g (0.72 mmol) of pyridinium p-toluenesulfonate. The resulting solution was stirred at ambient temperature for 16 h, washed sequentially with 10% citric acid, aqueous brine, and aqueous NaHCO$_3$, dried over Na$_2$SO$_4$, and concentrated in vacuo. The residue was purified by silica gel chromatography using 7:1 hexane:ethyl acetate to provide 1.13 g (87) of the desired compound ($R_f$ 0.64, 2:1 hexane:ethyl acetate). $^1$H NMR spectrum showed a 1:1 mixture of diastereomers. Mass spectrum: $(M+H)^+ = 362$.

EXAMPLE 11

(2S,3S)-3-(t-Butyloxycarbonylamino)-4-phenyl-2-((3,4,5,6-tetrahydropyran-2-yl)oxy)butanal Using the procedure of Example 4 with the resultant compound of Example 10 provided the desired compound.

EXAMPLE 12 trans-(4S,5S)-Methyl 5-(t-Butyloxycarbonylamino)-6-phenyl-4-((3,4,5,6-tetrahydropyran-2-yl)oxy)-2-hexenoate Using the procedure of Example 5 with the resultant compound of Example 11 provided, after silica gel chromatography using 6:1 hexane:ethyl acetate, the desired compound ($R_f$ 0.55, 7:3 hexane:ethyl acetate) in 69% yield. $^1$H NMR spectrum showed a 1:1 mixture of diastereomers. Mass spectrum: $(M+H)^+ = 420$.

EXAMPLE 13 trans-(4S,5S)-Methyl 5-(t-Butyloxycarbonylamino)-4-hydroxy-6-phenyl-2-hexenoate Using the procedure of Example 6 with the resultant compound of Example 12 provided, following silica gel chromatography using a gradient of 15–30% ethyl acetate in hexane, the desired compound (m.p. 108°–109° C., $R_f$ 0.44, 2:1 hexane:ethyl acetate) in 75% yield. $^1$H NMR (CDCl$_3$) 1.39 (s, 9 H), 2.96 (d, J=8 Hz, 2 H), 3.73 (s, 3 H), 3.75–3.85 (m, 2 H), 4.32 (br, 1 H), 4.79 (br d, 1 H), 6.11 (br d, J=15 Hz, 1 H), 6.94 (dd, J=15, 4 Hz, 1 H), 7.2–7.35 (m, 5 H). Mass spectrum: $(M+H)^+ = 336$.

EXAMPLE 14 trans-(4S,5S)-Methyl 5-(t-Butyloxycarbonylamino)-4-(methanesulfonyloxy)-6-phenyl-2-hexenoate Using the procedure of Example 7 with the resultant compound of Example 13 provided the crude desired compound in 58% yield. Mass spectrum: $(M+H)^+ = 414$.

EXAMPLE 15 trans-(2S,5S)-Methyl 2-Benzyl-5-(t-butyloxycarbonylamino)-6-phenyl-3-hexenoate Using the procedure of Example 8 but replacing the resultant compound of Example 7 with the resultant compound of Example 14 provided, after silica gel chromatography using 6:1 hexane:ethyl acetate, the desired compound (m.p. 84°-85° C., R0.73, 2:1 hexane:ethyl acetate) in 90% yield. $^1$H NMR (CDCl$_3$) 1.41 s, 9 H), 2.7–2.8 (m, 3 H), 3.01 (dd, J=14, 8 Hz, 1 H), 3.26 (q, J=7 Hz, 1 H), 3.61 (s, 3 H), 4.37 (m, 2 H), 5.42 (br d, 1 H), 5.56 (dd, J=15, 8 Hz, 1 H), 7.03–7.12 (m, 4 H), 7.2–7.3 (m, 6 H).

EXAMPLE 16

(3S,4S)-4-(t-Butyloxycarbonylamino)-3-(t-butyldimethylsilyloxy)-5-phenyl-1-pentene A solution of 1.0 g of the resultant compound of Example 9 and 0.49 g of imidazole in 10 ml of dimethylformamide was cooled to 0° C. and treated with 0.60 g of t-butyldimethylsilyl chloride. The resulting solution was stirred at ambient temperature for 6 h, diluted with ether, washed with brine, dried over $Na_2SO_4$, and concentrated in vacuo. The residue was purified by silica gel chromatography using 5:1 hexane:ethyl acetate to provide 1.35 g (96%) of the desired compound ($R_f$ 0.73, 3:1 hexane:ethyl acetate). $^1$H NMR (CDCl$_3$) δ 0.04 (s, 3 H), 0.09 (s, 3 H), 0.95 (s, 9 H), 1.36 (s, 9 H), 2.70 (m, 1 H), 2.88 (m, 1 H), 3.73 (m, 1 H), 3.87 (m, 1 H), 4.15 (m, 1 H), 5.1–5.2 (AA', 2 H), 5.84 (m, 1 H), 7.15–7.3 (m, 5 H). Mass spectrum: (M+H)$^+$ =450.

EXAMPLE 17

(2S,3S)-3-(t-Butyloxycarbonylamino)-2-(t-butyldimethylsilyloxy)-5-phenylbutanal

Using the procedure of Example 4 with the resultant compound of Example 16 provided the crude desired compound ($R_f$ 0.72, 2:1 hexane:ethyl acetate) in 80% yield.

EXAMPLE 18 trans-(4S,5S)-Methyl 5-(t-Butyloxycarbonylamino)-4-(t-butyldimethylsilyloxy)-6-phenyl-2-hexenoate Using the procedure of Example 5 with the resultant compound of Example 17 provided, after silica gel chromatography using 6:1 hexane:ethyl acetate, the desired compound ($R_f$ 0.68, 3:1 hexane:ethyl acetate) in 88% yield. $^1$H NMR (CDCl$_3$) δ 0.05 (s, 3 H), 0.12 (s, 3 H), 0.97 (s, 9 H), 1.35 (s, 9 H), 2.57 (dd, J=14, 9 Hz, 1 H), 2.94 (dd, J=14, 6 Hz, 1 H), 3.73 (s, 3 H), 3.95 (m, 1 H), 4.42 (m, H), 4.61 (br d, 1 H), 6.00 (dd, 15, 1 Hz, 1 H), 6.96 (dd, J=15, 6 Hz, 1 H), 7.15–7.3 (m, 5 H).

EXAMPLE 19 trans-(4S,5S)-Methyl 5-(t-Butyloxycarbonylamino)-4-hydroxy-6-phenyl-2-hexenoate

A solution of 1.0 g (2.2 mmol) of the resultant compound of Example 18 in 8 ml of tetrahydrofuran was treated with 2.2 ml (2.2 mmol) of a 1.0M solution of tetra-n-butylammonium fluoride in tetrahydrofuran. After being stirred under N$_2$ atmosphere at ambient temperature for 2 h, the solution was concentrated in vacuo, and the residue was partitioned between ethyl acetate and brine. The organic layer was washed with brine, dried over Na$_2$SO$_4$, and concentrated in vacuo. Chromatography of the residue on silica gel using 4:1 hexane:ethyl acetate provided 0.36 g (47%) of the desired compound.

EXAMPLE 20 trans-(2R,5S)-Methyl 5-(t-Butyloxycarbonylamino)-2-cyclohexyl-6-phenyl-3-hexenoate Using the procedure of Example 8 but replacing benzylmagnesium chloride with cyclohexylmagnesium chloride (2.0M solution in ether) provided, after chromatography on silica gel using 6:1 hexane:ethyl acetate, the desired compound ($R_f$ 0.71, 2:1 hexane:ethyl acetate) in 87% yield. $^1$H NMR (CDCl$_3$) δ 0.7–1.7 (br envelope, 11 H), 1.41 (s, 9 H), 2.69 (m, 1 H), 2.83 (m, 2 H), 3.64 (s, 3 H), 4.41 (m, 2 H), 5.47 (AA', 2 H), 7.1–7.3 (m, 5 H).

EXAMPLE 21 trans-(2S,5S)-Methyl 5-(t-Butyloxycarbonylamino)-2-cyclohexyl-6-phenyl-3-hexenoate Using the procedure of Example 8 but replacing benzylmagnesium chloride with cyclohexylmagnesium chloride (2.0M solution in ether) and replacing the resultant compound of Example 7 with the resultant compound of Example 14 provided, after chromatography on silica gel using 6:1 hexane:ethyl acetate, the desired compound ($R_f$ 0.65, 2:1 hexane:ethyl acetate) in 82% yield. $^1$H NMR (CDCl$_3$) δ 0.6–1.7 (br envelope, 11 H), 1.41 (s, 9 H), 2.69 (m, 1 H), 2.75 (dd, J=14, 7 Hz, 1 H), 2.89 (dd, J=14, 5 Hz, 1 H), 3.66 (s, 3 H), 4.41 (m, 2 H), 5.44 (AA', 2 H), 7.1–7.3 (m, 5 H). Mass spectrum: (M+H)$^+$ =402.

EXAMPLE 22 trans-(2S,5R)-Methyl 2-(t-Butyloxycarbonylamino)-7-methyl-1-phenyl-3-hexen-5-carboxylate Using the procedure of Example 8 but replacing benzylmagnesium chloride with isobutylmagnesium chloride (2.0M solution in tetrahydrofuran) provided, after chromatography on silica gel using 6:1 hexane:ethyl acetate, the desired compound ($R_f$ 0.78, 2:1 hexane:ethyl acetate) in 80% yield. $^1$H NMR (CDCl$_3$) δ 0.81 (d, J=6 Hz, 3 H), 0.84 (d, J=6 Hz, 3 H), 1.25–1.45 (m, 3 H), 1.41 (s, 9 H), 2.77 (dd, J=14, 7 Hz, 1 H), 2.87 (dd, J=14, 6 Hz, 1 H), 3.04 (q, J=7 Hz, 1 H), 3.65 (s, 3 H), 4.4 (br m, 2 H), 5.46 (AA', 2 H), 7.15–7.3 (m, 5 H). Mass spectrum: (M+H)$^+$ =376.

EXAMPLE 23 trans-(5S,2S)-Methyl 2-(t-Butyloxycarbonylamino)-7-methyl-1-phenyl-3-hexen-5-carboxylate Using the procedure of Example 8 but replacing benzylmagnesium chloride with isobutylmagnesium chloride (2.0M solution in tetrahydrofuran) and replacing the resultant compound of Example 7 with the resultant compound of Example 14 provided, after chromatography on silica gel using 6:1 hexane:ethyl acetate, the desired compound ($R_f$ 0.86, 2:1 hexane:ethyl acetate) in 77% yield. $^1$H NMR (CDCl$_3$) δ 0.83 (d, J=7 Hz, 3 H), 0.87 (d, J=7 Hz, 3 H), 1.3–1.55 (m, 3 H), 1.41 (s, 9 H), 2.82 (AA', 2 H), 3.05 (q, J=7 Hz, 1 H), 3.63 (s, 3 H), 4.40 (br m, 2 H), 5.48 (AA', 1 H), 7.13–7.3 (m, 5 H).

EXAMPLE 24 trans-(1R,4S)-Methyl 4-(t-Butyloxycarbonylamino)-1,5-diphenyl-2-pentenoate

Using the procedure of Example 8 but replacing benzylmagnesium chloride with phenylmagnesium chloride (3.0M solution in tetrahydrofuran) provided, after chromatography on silica gel using 6:1 hexane:ethyl acetate, the desired compound ($R_f$ 0.70, 3:1 hexane:ethyl acetate) in 78% yield. $^1$H NMR (CDCl$_3$) δ 1.39 (s, 9 H), 2.82 (m, 2 H), 3.67 (s, 3 H), 4.28 (d, J=8 Hz, 1 H), 4.43

(br, 2 H), 5.51 (dd, J=16, 5 Hz, 1 H), 5.89 (dd, J=16, 8 Hz, 1 H), 7.1–7.35 (m, 10 H). Mass spectrum: (M+H)+ =396.

EXAMPLE 25 trans-(4'S,5'S)-Ethyl 3-(3-(t-Butyloxycarbonylamino)-4-(cyclohexylmethyl)-2,2-dimethyloxazolidin-5-yl)-propenoate A suspension of 0.42 g (10.5 mmol) of sodium hydride (60% oil dispersion) in 80 ml of anhydrous tetrahydrofuran was cooled under $N_2$ atmosphere to 0° C. and treated with 2.1 ml (10.5 mmol) of triethylphosphonacetate. The resulting solution was stirred for 10 min, treated with a solution of 2.80 g (8.6 mmol) of 3-(t-butyloxycarbonylamino)-4-(cyclohexylmethyl)-2,2-dimethyloxazolidin-5-carboxaldehyde in 20 ml of tetrahydrofuran. After being stirred for 45 min, the solution was quenched with aqueous ammonium chloride, extracted with ether, dried over $MgSO_4$, and concentrated in vacuo. Silica gel chromatography of the residue using 12:1 hexane:ethyl acetate provided 3.05 g (90%) of the desired compound ($R_f$ 0.25, 9:1 hexane:ethyl acetate) as an oil. $^1H$ NMR ($CDCl_3$) δ 0.9–1.8 (br envelope, 13 H), 1.31 (t, J=7 Hz, 3 H), 1.48 (s, 9 H), 1.53 (s, 3 H), 1.61 (s, 3 H), 3.89 (m, 1 H), 4.22 (q, J=7 Hz, 2 H), 4.44 (ddd, J=6, 3, 1.5 Hz, 1 H), 6.07 (dd J=16, 2 Hz, 1 H), 6.95 (dd, J'16, 6 Hz, 1 H). Mass spectrum: (M+H)+ =3.96.

Anal. Calcd for $C_{22}H_{37}NO_5$: C, 66.81; H, 9.43; N, 3.54. Found: C, 67.45; H, 9.50; N, 3.56.

EXAMPLE 26 trans-(4S,5S)-Ethyl 5-(t-Butyloxycarbonylamino)-5-cyclohexyl-4-hydroxy-2-hexenoate A solution of 2.95 g (7.47 mmol) of the resultant compound of Example 25 and 0.48 g (2.5 mmol) of p-toluenesulfonic acid monohydrate in 50 ml of ethanol was stirred at ambient temperature for 8 h. The resulting solution was treated with aqueous $NaHCO_3$, concentrated in vacuo to a small volume, extracted with ether, washed with saturated brine, dried over $MgSO_4$, and concentrated. Silica gel chromatography using 30% ethyl acetate in hexane provided 2.22 g (84%) of the desired compound ($R_f$ 0.25, 15% ethyl acetate in chloroform). $^1H$ NMR ($CDCl_3$) δ 0.8–1.7 (br envelope, 13 H), 1.29 (t, J=7 Hz, 3 H), 1.42 (s, 9 H), 2.32 (br, 1 H), 3.71 (m, 1 H), 4.20 (q, J=7 Hz, 2 H), 4.29 (m, 1 H), 4.59 (br d, 1 H), 6.09 (dd, J=16, 2 Hz, 1 H), 6.95 (dd, J=16, 5 Hz, 1 H). Mass spectrum: (M+H)+ =356.

EXAMPLE 27 trans-(4S,5S)-Ethyl 5-(t-Butyloxycarbonylamino)-6-cyclohexyl-4-(methanesulfonyloxy)-2-hexenoate Using the procedure of Example 7 but replacing the resultant compound of Example 6 with the resultant compound of Example 26 provided the crude desired compound ($R_f$ 0.44, 15% ethyl acetate in chloroform) in 89% yield. $^1H$ NMR ($CDCl_3$) δ 0.8–1 (br envelope, 13 H), 1.30 (t, J=7 Hz, 3 H), 1.44 (s, 9 H), 3.05 (s, 3 H), 4.01 (m, 1 H), 4.21 (q, J=7 Hz, 2 H), 4.47 (br d, J=10 Hz, 1 H), 5.10 m, 1 H), 6.13 (dd, J=16, 1.5 Hz, 1 H), 6.89 (dd, J=16, 6 Hz, 1 H). Mass spectrum: (M+NH4)+ =451.

EXAMPLE 28 trans-(2S,5S)-Ethyl 2-(t-Butyloxycarbonylamino)-1-cyclohexyl-3-hexen-5-carboxylate Using the procedure of Example 8 but replacing benzylmagnesium chloride with n-propylmagnesium chloride and replacing the resultant compound of Example 7 with the resultant compound of Example 27 provided, after silica gel chromatography using 15% ethyl acetate in hexane, the desired compound ($R_f$ 0.35, 4:1 hexane:ethyl acetate) in 6% yield. $^1H$ NMR ($CDCl_3$) δ 0.8–1.0 (m, 2 H), 0.90 (t, J=7 Hz, 3 H), 1.1–1.8 (br envelope, 15 H), 1.43 (s, 9 H), 2.97 (q, J=8 Hz, 1 H), 4.12 (q, J=7 Hz, 2 H), 4.33 (m, H), 5.43 (br d, 1 H), 5.56 (dd, J=16, 9 Hz, 1 H). $^{13}C$ NMR ($CDCl_3$, ppm) 13.77, 14.22, 20.24, 26.25, 26.30, 26.53, 28.38 (3 C), 33.16, 34.19, 34.65, 43.31, 48.72, 49.46, 49.50, 60.43, 127.89, 133.83, 174.33. Mass spectrum: (M+H)+ =382.

EXAMPLE 29

N-(t-Butyloxycarbonyl)-L-leucine N-Methoxy-N-methylamide

A mixture of 8.30 g (34.6 mmol) of N-(t-butyloxycarbonyl)-L-leucine, 4.03 g (41.5 mmol) of methoxyamine hydrochloride, 5.60 g (41.5 mmol) of 1-hydroxybenzotriazole, 8.55 g (41.5 mmol) of dicyclohexylcarbodiimide, and 4.56 ml (41.5 mmol) of 4-methylmorpholine in 200 ml of dichloromethane was stirred at ambient temperature for 24 h. The resulting mixture was filtered, and the filtrate was concentrated in vacuo. The residue was partitioned between ethyl acetate and 1N HCl, and the organic phase was washed sequentially with aqueous $NaHCO_3$ and saturated brine, dried over $MgSO_4$, and concentrated in vacuo. Silica gel chromatography using 30% ethyl acetate in hexane provided 7.16 g (76%) of the desired compound ($R_f$ 0.21, 3:1 hexane:ethyl acetate).

EXAMPLE 30

(4S)-4-(t-Butyoxycarbonylamino)-6-methyl-1-hepten-3-one

A solution of 1.01 g (3.69 mmol) of the resultant compound of Example 29 in 50 ml of anhydrous tetrahydrofuran was cooled under $N_2$ atmosphere to −78° C. and treated with 16 ml (9.6 mmol) of vinylmagnesium bromide (0.6M in tetrahydrofuran). The resulting solution was allowed to warm to ambient temperature, stirred for 1.5 h, and poured over a mixture of ice and 10% aqueous citric acid. The mixture was extracted with ether, washed with saturated brine, dried over $MgSO_4$, and concentrated in vacuo. Silica gel chromatography of the residue using 12% ethyl acetate in hexane provided 0.48 g (58%) of the desired compound ($R_f$ 0.48, 7:3 hexane:ethyl acetate). $^1H$ NMR ($CDCl_3$) δ 0.93 (d, J=7 Hz, 3 H), 1.00 (d, J=7 Hz, 1 H), 1.3–1.45 (m, 2 H), 1.43 (s, 9 H), 1.74 (m, 1 H), 4.65 (td, J=9, 4 H, 1 H), 5.09 (br d, 1 H), 5.88 (dd, J=10, 2 Hz, 1 H), 6.38 (dd, J=18, 2 Hz, 1 H), 6.48 (dd, J=18, 10 Hz, 1 H). Mass spectrum: (M+H)+ =242.

EXAMPLE 31

(3R,4S)-4-(t-Butyloxycarbonylamino)-3-hydroxy-6-methyl-1-heptene

A solution of the resultant compound of Example 30 (3.25 g, 14.4 mmol) in anhydrous tetrahydrofuran was cooled to −78° C. and treated slowly along the side of the reaction vessel with 57 ml (57 mmol) of diisobutylaluminum hydride (1M in tetrahydrofuran). The solution was stirred at −78° C. for 0.5 h, quenched cautiously with methanol, allowed to warm to ambient temperature, and partitioned between ether and aqueous Rochelle salts. The organic phase was washed sequentially with water and brine, dried over MgSO4, and concentrated in vacuo. Chromatography on silica gel using 4:1 hexane:ethyl acetate provided 0.77 g (22%) of the desired compound (10:1 ratio of (3S,4S):(3R:4S) isomers). $^1$H NMR (CDCl3) δ 0.91 (d, J=7 Hz 3 H), 0.94 (d, J=7 Hz, 3 H), 1.26 (br t, J=7 Hz, 2 H), 1.44 (s, 9 H), 1.67 (nonet J=7 Hz, 1 H), 2.96 (br d, J=5 Hz, 1 H), 3.82 (m, 1 H), 4.18 (m, 1 H), 4.50 (br d, 1 H), 5.23 (dt, J=11, 1.5 Hz, 1 H), 5.33 (dt, J=17, 1.5 Hz, 1 H), 5.84 (ddd, J=17, 11, 6 Hz, 1 H).

EXAMPLE 32

(3R, 4S)-4-(t-Butyloxycarbonylamino)-3-(methanesulfonyloxy)-6-methyl-1-heptene

A solution of 0.29 g (1.19 mmol) of the resultant compound of Example 31 and 0.25 ml (1.8 mmol) of triethylamine in 7 ml of dichloromethane was cooled to 0° C. and treated with 0.12 ml (1.55 mmol) of methanesulfonyl chloride. After 45 min, the solution was diluted with ether, washed sequentially with 10% aqueous citric acid, aqueous NaHCO3 and saturated brine, dried over MgSO4, and concentrated in vacuo. Silica gel chromatography of the residue using 3:1 hexane:ethyl acetate provided 0.23 g (61%) of the desired compound (R$_f$ 0.48, 3:2 hexane:ethyl acetate).

EXAMPLE 33 trans-(4R,5S)-Methyl 5-(t-Butyloxycarbonylamino)-4-(methanesulfonyloxy)-7-methyl-2-octenoate A solution of 0.22 g (0.69 mmol) of the resultant compound of Example 32 in 15 ml of dichloromethane was cooled to −78° C. and treated with a stream of O3 in air until the blue color persisted. The solution was subsequently purged with air until the blue color was discharged, treated with 0.5 ml of dimethylsulfide, allowed to warm to ambient temperature over 40 min, and treated with 0.29 g (0.87 mmol) of methyl (triphenylphosphoranylidene)acetate. The resulting solution was stirred at ambient temperature for 4 h, concentrated in vacuo, partitioned between dichloromethane and water, dried over MgSO4, and concentrated. Silica gel chromatography using 30% ethyl acetate in hexane provided 0.08 g (31%) of the desired compound (R$_f$ 0.17, 30% ethyl acetate in hexane). $^1$H NMR (CDCl3) δ 0.89 (d, J=7 Hz, 3 H), 0.93 (d, J=7 Hz, 3 H), 1.22 (m, 2 H), 1.44 (s, 9 H), 1.69 (m, 1 H), 3.06 (s, 3 H), 3.78 (s, 3 H), 3.92 (m, 1 H), 4.58 (br d, 1 H), 5.40 (m, 1 H), 6.16 (dd, J=15, 2 Hz, 1 H), 6.87 (dd, J=15, 6 Hz, 1 H). Mass spectrum: (M+H)+ =380.

EXAMPLE 34 trans-(3R,6S)-Methyl 6-(t-Butyloxycarbonylamino)-2,8-dimethyl-4-nonen-3-carboxylate Using the procedure of Example 8 but replacing benzylmagnesium chloride with isopropylmagnesium chloride and replacing the resultant compound of Example 7 with the resultant compound of Example 33 provided the desired compound.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A substantially pure (4R,5S), (4R,5R), (4,5S) or (4S,5R) diastereomer of the compound of the formula:

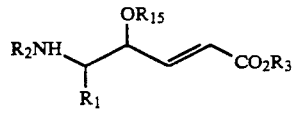

wherein $R_1$ is loweralkyl, cycloalkyl, cycloalkylalkyl, aryl, arylalkyl, alkoxyalkyl or thioalkoxyalkyl; $R_2$ is an N-protecting group; $R_3$ is loweralkyl, benzyl, substituted benzyl wherein the phenyl ring is substituted with one, two or three substituents independently selected from loweralkyl, alkoxy and halo or $R_3$ is t-butyldimethylsilyl, t-butyldiphenylsilyl, triethylsilyl or triisopropylsilyl; and $R_{15}$ is hydrogen, an O-protecting group or —SO2R4 wherein R4 is loweralkyl, haloalkyl, phenyl or substituted phenyl wherein the phenyl ring is substituted with loweralkyl or halo.

2. The compound of claim 1 wherein $R_1$ is loweralkyl, cycloalkylalkyl or arylalkyl; $R_{15}$ is —SO2R4 wherein R4 is loweralkyl, haloalkyl, phenyl or substituted phenyl wherein the phenyl ring is substituted with loweralkyl or halo; and $R_3$ is loweralkyl.

* * * * *

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 3, LINE 28,

REPLACE 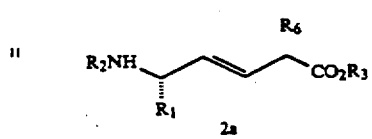 WITH 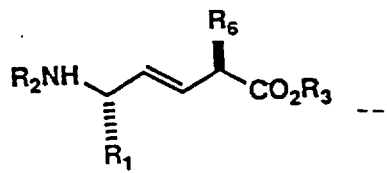 --

COLUMN 3, LINE 35:

REPLACE 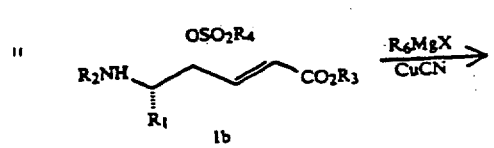 WITH 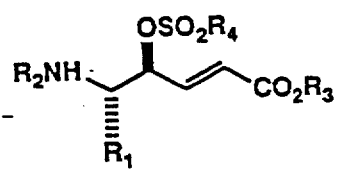 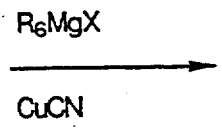 --

COLUMN 3, LINE 45:

REPLACE 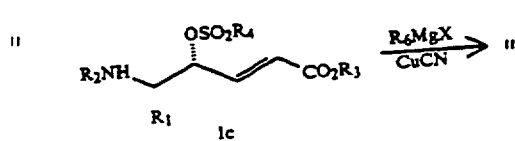 WITH 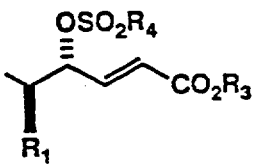 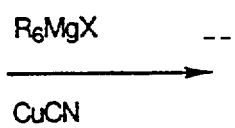 --

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 3, LINE 53:
REPLACE

" 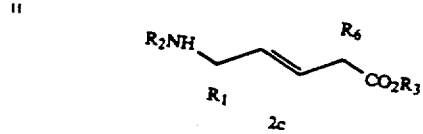 "   WITH   -- 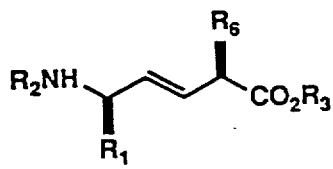 --

COLUMN 3, LINE 60:
REPLACE

" 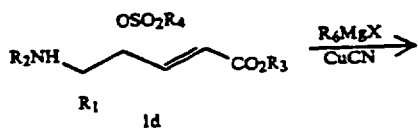 "   WITH   -- 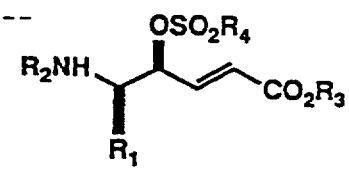 --

COLUMN 3, LINE 65:
REPLACE

" 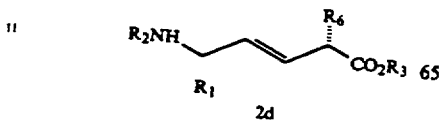 "   WITH   -- 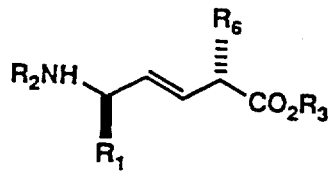 --

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 4, LINE 12:
REPLACE                     WITH

" 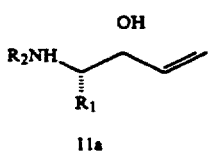 "    -- 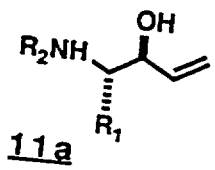 --

COLUMN 4, LINE 50:
REPLACE                     WITH

" 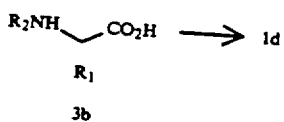 <u>1d</u> "    -- 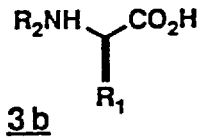 --

COLUMN 4, LINE 57:
REPLACE                     WITH

" 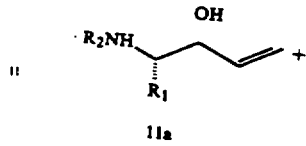 "    -- 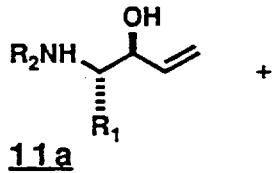 --

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 5, LINE 5:
REPLACE          WITH

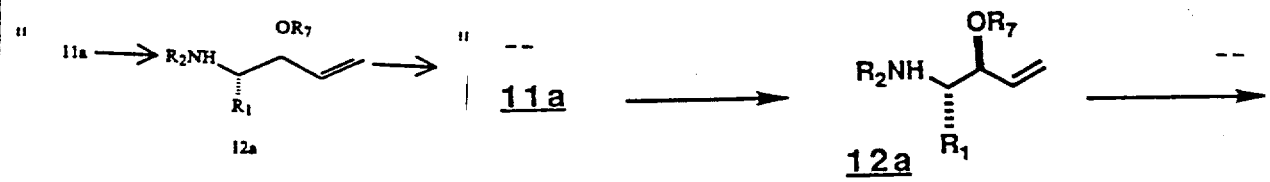

COLUMN 5, LINE 10:
REPLACE          WITH

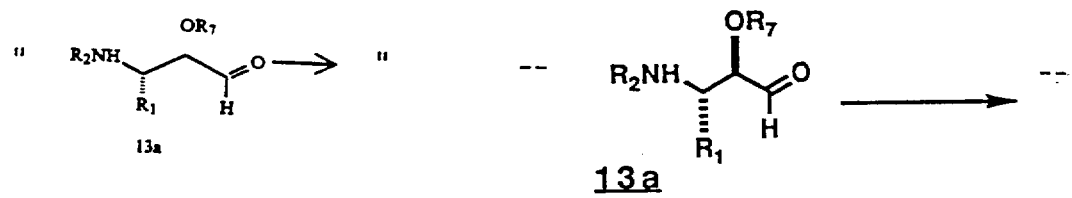

COLUMN 5, LINE 18:
REPLACE          WITH

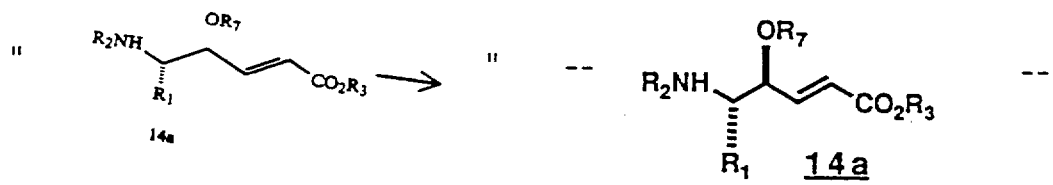

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 5, LINE 25:
   REPLACE                     WITH

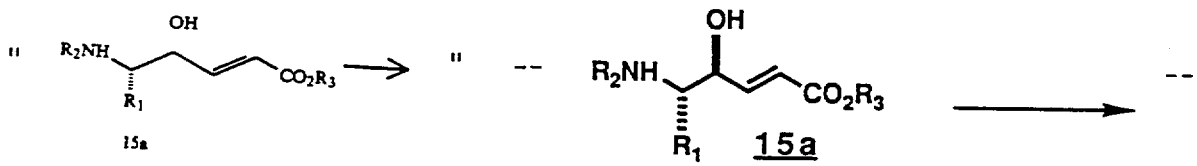

COLUMN 5, LINE 30:
   REPLACE                     WITH

COLUMN 5, LINE 36:
   REPLACE                     WITH

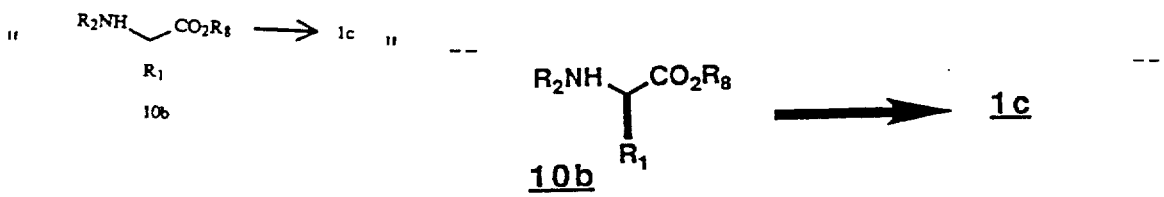

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 5, LINE 46:
REPLACE                    WITH

" 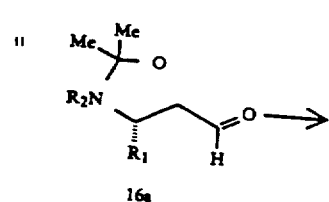  →   "  --  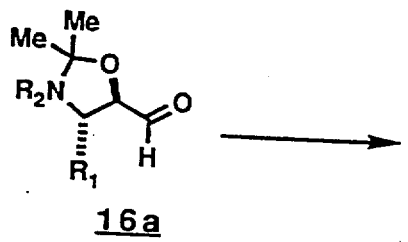  →  --

COLUMN 5, LINE 55:
REPLACE                    WITH

" 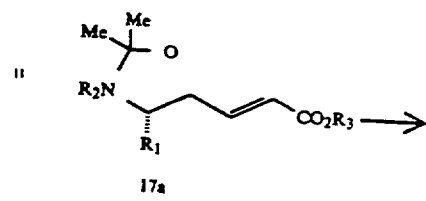  →   "  --  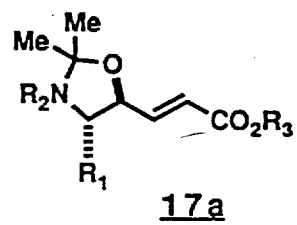  --

COLUMN 5, LINE 65:
REPLACE                    WITH

" 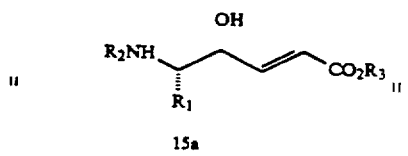  "   --  →  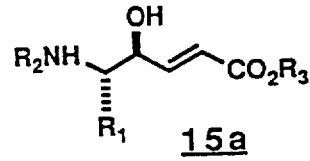  --

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 6, LINE 25:
REPLACE

"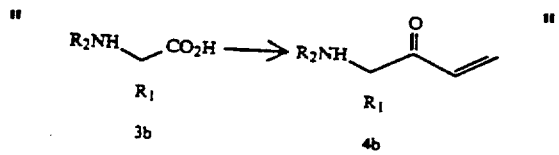"

WITH

—  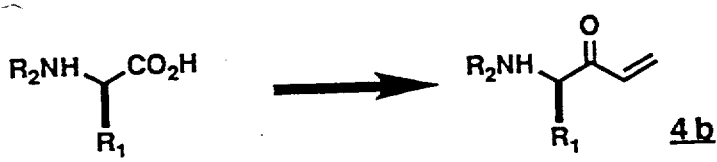  —

COLUMN 6, LINE 55:
REPLACE

"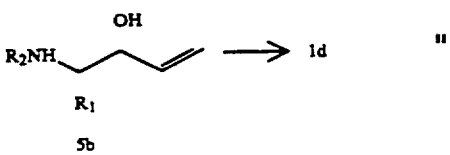"

WITH

—  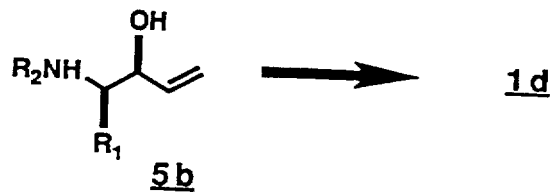  —

UNITED STATES PATENT AND TRADEMARK OFFICE
CERTIFICATE OF CORRECTION

PATENT NO. : 5,130,468
DATED : July 14, 1992
INVENTOR(S) : Dale J. Kempf

It is certified that error appears in the above-identified patent and that said Letters Patent is hereby corrected as shown below:

COLUMN 6, LINE 65:
REPLACE                             WITH

"  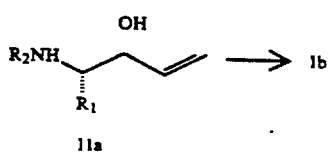  "          "  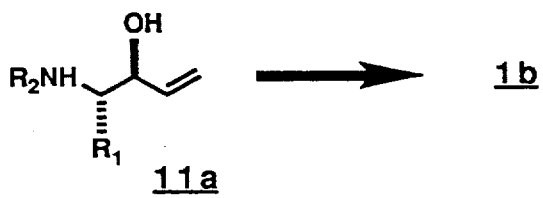  --

COLUMN 7, LINE 5:
REPLACE                             WITH

"  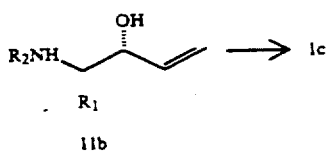  "          "  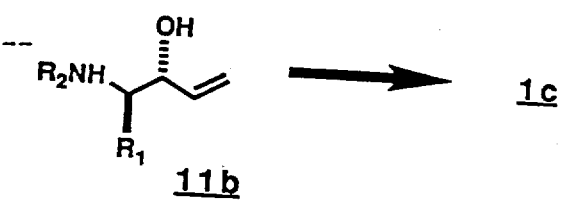  --

COLUMN 18, LINE 27:        REPLACE "(4R,5S), (4R,5R), (4,5S)"
                           with -- (4R,5S), (4R,5R), (4S,5S)--

UNITED STATES PATENT AND TRADEMARK OFFICE
CERTIFICATE OF CORRECTION

PATENT NO. : 5,130,468

DATED : July 4, 1992

INVENTOR(S) : Dale J. Kempf

It is certified that error appears in the above-indentified patent and that said Letters Patent is hereby corrected as shown below:

COLUMN 18, LINE 27:   REPLACE "(4R,5S), (4R,5R)" with --(4R,5S), (4R,5R), (4S.5S)--.

Signed and Sealed this

Twenty-second Day of November, 1994

Attest:

BRUCE LEHMAN

Attesting Officer      Commissioner of Patents and Trademarks